United States Patent
Coe et al.

(10) Patent No.: US 7,641,652 B2
(45) Date of Patent: Jan. 5, 2010

(54) BAND LIGATION AND COAGULATION

(75) Inventors: Jonathan Coe, Cincinatti, OH (US);
Omar Vakharia, Cincinnati, OH (US);
Gary Long, Cincinnati, OH (US);
Rudolph Nobis, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 475 days.

(21) Appl. No.: 11/427,598

(22) Filed: Jun. 29, 2006

(65) Prior Publication Data
US 2008/0004622 A1 Jan. 3, 2008

(51) Int. Cl.
*A61B 18/18* (2006.01)
(52) U.S. Cl. .............. 606/49; 606/41; 606/50
(58) Field of Classification Search ........... 606/41, 606/46–50, 139–144, 148
See application file for complete search history.

(56) References Cited

U.S. PATENT DOCUMENTS

| | | | |
|---|---|---|---|
| 3,870,048 A | 3/1975 | Yoon | |
| 4,257,419 A | 3/1981 | Goltner et al. | |
| 5,336,222 A | 8/1994 | Durgin, Jr. et al. | |
| 5,507,797 A * | 4/1996 | Suzuki et al. | 606/140 |
| 5,906,594 A | 5/1999 | Scarfone et al. | |
| 5,968,056 A * | 10/1999 | Chu et al. | 606/140 |
| 5,997,533 A | 12/1999 | Kuhns | |
| 6,050,995 A * | 4/2000 | Durgin | 606/47 |
| 6,099,535 A | 8/2000 | Lamport et al. | |
| 6,436,108 B1 * | 8/2002 | Mears | 606/140 |

FOREIGN PATENT DOCUMENTS

| | | |
|---|---|---|
| EP | 1147744 | 10/2001 |
| WO | 0182847 | 11/2001 |
| WO | WO-2004021865 | 3/2004 |

OTHER PUBLICATIONS

Cipolletta, et al., "Argon plasma coagulation prevent variceal recurrence after band ligation of esophageal varices: preliminary results of a prospective randomized trial," vol. 56, Nov. 4, 2002 (467-471), Goastrointestinal Endoscopy.
International Search Report for EP 07 25 2618 mailed Jun. 11, 2007.

* cited by examiner

*Primary Examiner*—Roy D Gibson
(74) *Attorney, Agent, or Firm*—Nutter McClennen & Fish LLP

(57) ABSTRACT

Devices and methods for ligating and coagulating tissue are provided. In one embodiment, a device is provided having an end effector that is adapted to access tissue to be treated at a surgical site and has the capability to both ligate and coagulate the targeted tissue. The end effector can include at least one ligation band that is removably disposed in a delivery configuration on a portion of the end effector and is adapted to be configured in a tissue-engaging configuration upon release from the end effector. The end effector can also include a pair of spaced electrodes disposed adjacent to each other on a tissue contacting portion of the end effector.

22 Claims, 11 Drawing Sheets

BAND LIGATION AND COAGULATION

FIELD OF THE INVENTION

The present invention relates to devices and methods for ligating vessels and coagulating tissue.

BACKGROUND OF THE INVENTION

Ligation is a well known technique for treating various types of tissue defects and lesions including varices and hemorrhoids. A target region of tissue containing the vessel can be ligated by applying an elastic cord or band to the tissue. The band stops the circulation of blood through the vessel and causes the ligated tissue to necrose and slough off. Ligation has proved to be somewhat successful in the treatment of esophageal varices.

Esophageal varices are dilated or enlarged blood vessels within the wall of the esophagus. Esophageal varices are most frequently found in the lower part of the esophagus and are usually the result of obstructed blood flow through the portal vein, which carries blood from the intestine and the spleen to the liver. A common cause of this obstruction is liver disease, such as cirrhosis. For example, patients with cirrhosis develop portal hypertension which causes blood flow through the liver to be diminished. As blood flow through the liver is decreased, blood flow through the microscopic blood vessels within the esophageal wall is increased. This increase in flow causes the blood vessels to dilate. In some cases, an esophageal varix can be as large as 0.5 to 1.0 cm or larger in diameter. Other causes of esophageal varices include blood clots in the portal vein and any condition that increases pressure in the portal vein such as severe congestive heart failure. Esophageal varices cause no symptoms until they become large enough to rupture and bleed. Bleeding from esophageal varices is a life-threatening condition that requires immediate medical treatment.

Endoscopic variceal ligation is an established procedure used to treat esophageal varices before a rupture occurs and is based on a technique initially used for the band ligation of hemorrhoids. This technique involves applying small, elastic "O" rings or bands to a target region of tissue to thereby mechanically ligate and strangulate the variceal channels. The application of the ligation bands to a varix is typically accomplished by means of a device attached to a distal end of an endoscope. Endoscopic variceal ligation is somewhat successful at treating esophageal varices, but one drawback of endoscopic variceal ligation is that varices frequently recur after being treated.

While several devices are available for performing various ligation procedures, a need exists for methods and devices for ligating and coagulating a target region of tissue.

SUMMARY OF THE INVENTION

The present invention generally provides devices and methods for ligating and coagulating tissue. In one embodiment, a surgical device is provided having an end effector, at least one ligation band, and a pair of spaced electrodes. The end effector can be adapted to access tissue at a surgical site. The at least one ligation band can be removably disposed in a delivery configuration on a portion of the end effector, and the band can be adapted to be configured in a tissue-engaging configuration upon release from the end effector. In one embodiment, the ligation band can be an elastic ring. The pair of spaced electrodes can be disposed adjacent to each other on a tissue contacting portion of the end effector.

The end effector can have a variety of configurations and can be formed on, attached to, or removably matable to a distal end of an endoscope, accessory channel adapted to mate to an endoscope, or sleeve adapted to mate to an endoscope and/or accessory channel. In one embodiment, the end effector can include a cylindrical member having an outer wall defining a substantially central opening. The pair of electrodes can be disposed on a distal surface of the outer wall of the cylindrical member. The electrodes can be in communication with a current source that is adapted to be selectively energized.

In one embodiment, the end effector can be removably associated with an endoscope such that a central axis of the central opening is substantially transverse to a longitudinal axis of the endoscope. The end effector can also be movable and adapted to be oriented at a selected angle with respect to a longitudinal axis of the device. The device can also be associated with a suction line that is adapted to draw tissue into the central opening of the end effector.

The end effector can further include a cylindrical cap that is rotatably coupled to the cylindrical member such that rotating the cap is effective to release the at least one ligation band from the end effector. The device can also include an actuator that is operatively associated with the cap and is adapted to rotate the cap. In one embodiment, the actuator can be a pull wire having a portion that is wound around the cap and a proximally extending portion that can be manipulated by a user.

In a further embodiment, the at least one ligation band can be supported in its expanded condition by a frangible ring. The frangible ring can be threadably coupled to the end effector and can be adapted to collapse under the stress applied by the ligation band upon release from the end effector. In this embodiment, the electrodes can be disposed on a portion of the frangible ring. In another embodiment, the end effector can include a flexible membrane that is adapted to release at least one ligation band.

In another aspect of the invention, a method of ligating and coagulating tissue is provided and includes inserting an end effector translumenally, positioning the end effector adjacent a target region of tissue, drawing the target tissue into the opening, deploying at least one of the ligation bands to the target tissue to ligate the target tissue, and delivering current to the target tissue through the electrodes to thereby coagulate the target tissue. Alternatively, another method of ligating and coagulating tissue involves inserting an end effector translumenally, positioning the end effector adjacent a target region of tissue, drawing the target tissue into the opening, delivering current to the target tissue to thereby coagulate the target tissue, and deploying at least one of the ligation bands to the target tissue to ligate the target tissue. In one embodiment, the target tissue can be drawn into the opening by applying suction to the tissue. Deploying at least one of the ligation bands can include actuating a cylindrical cap threadably coupled to the end effector, and actuating the cylindrical cap can include, for example, rotating the cap using a pull wire wound around the cap. In one embodiment, deploying at least one of the ligation bands and delivering current to the target tissue can occur simultaneously. In another embodiment, deploying at least one of the ligation bands and delivering current to the target tissue can occur sequentially. The method can further include the step of sterilizing the device after at least one use.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for ligating and coagulating tissue. The methods and devices utilize an end effector that is adapted to access tissue to be treated at a surgical site and has the capability to both ligate and coagulate the targeted tissue. The end effector can include at least one ligation band that is removably disposed in a delivery configuration on a portion of the end effector and is adapted to be configured in a tissue-engaging configuration upon release from the end effector. The end effector can also include a pair of spaced electrodes disposed adjacent to each other on a tissue contacting portion of the end effector. The end effector can be incorporated into a variety of devices. For example, in one embodiment the end effector can be formed on, attached to, or removably matable to or deliverable through a distal end of an endoscope for ligating and/or coagulating a target region of tissue. In another embodiment, the end effector can be formed on, attached to, or removably matable to or deliverable through a distal end of an accessory channel adapted to mate to an endoscope, or sleeve adapted to mate to an endoscope and/or accessory channel. A person skilled in the art will appreciate that the end effector can be used with a variety of surgical tools and devices, including various other endoscopic and laparoscopic tools and devices, as well as tools and devices used in other surgical procedures.

Figure 1:
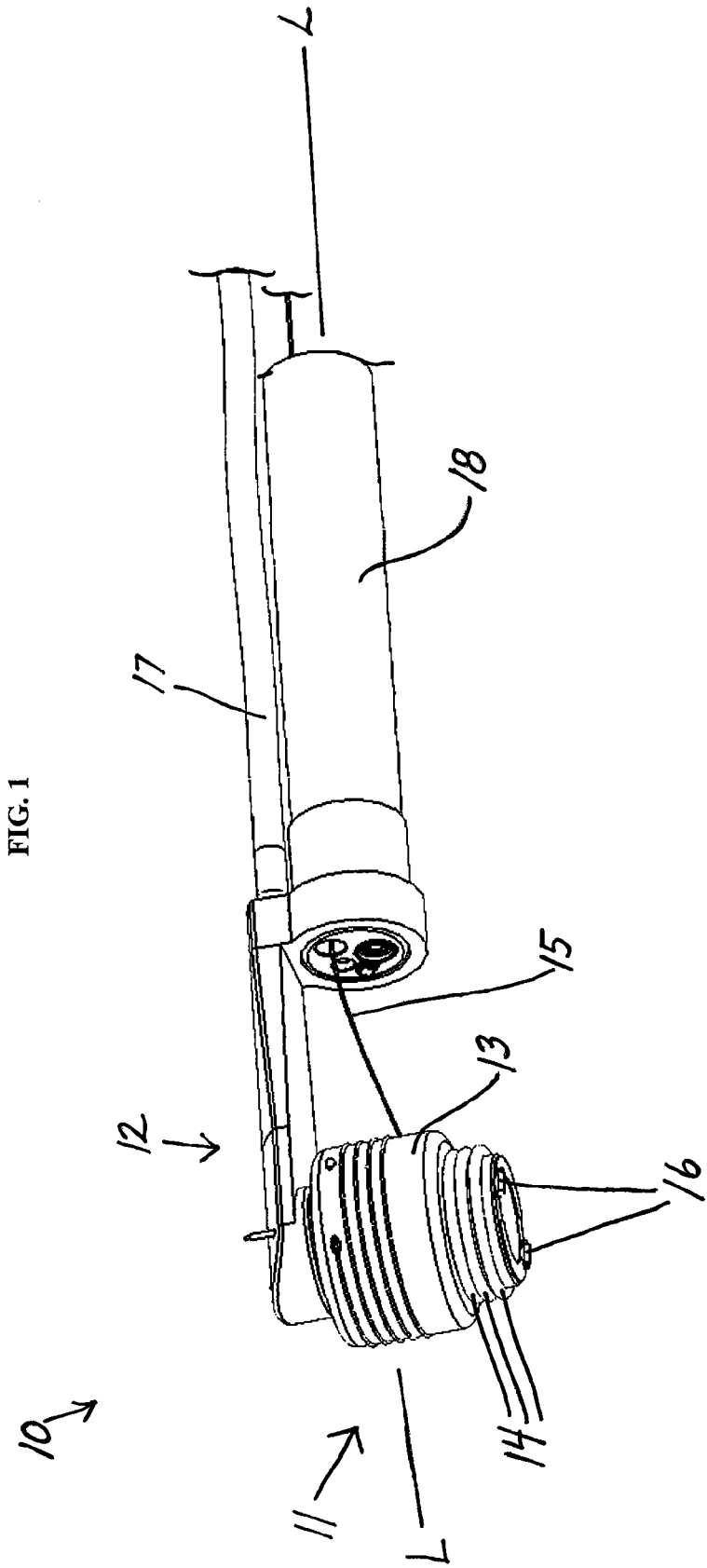
FIG. 1 is a perspective view of one embodiment of a ligation and coagulation device showing the device coupled to an endoscope.
Figure 2:
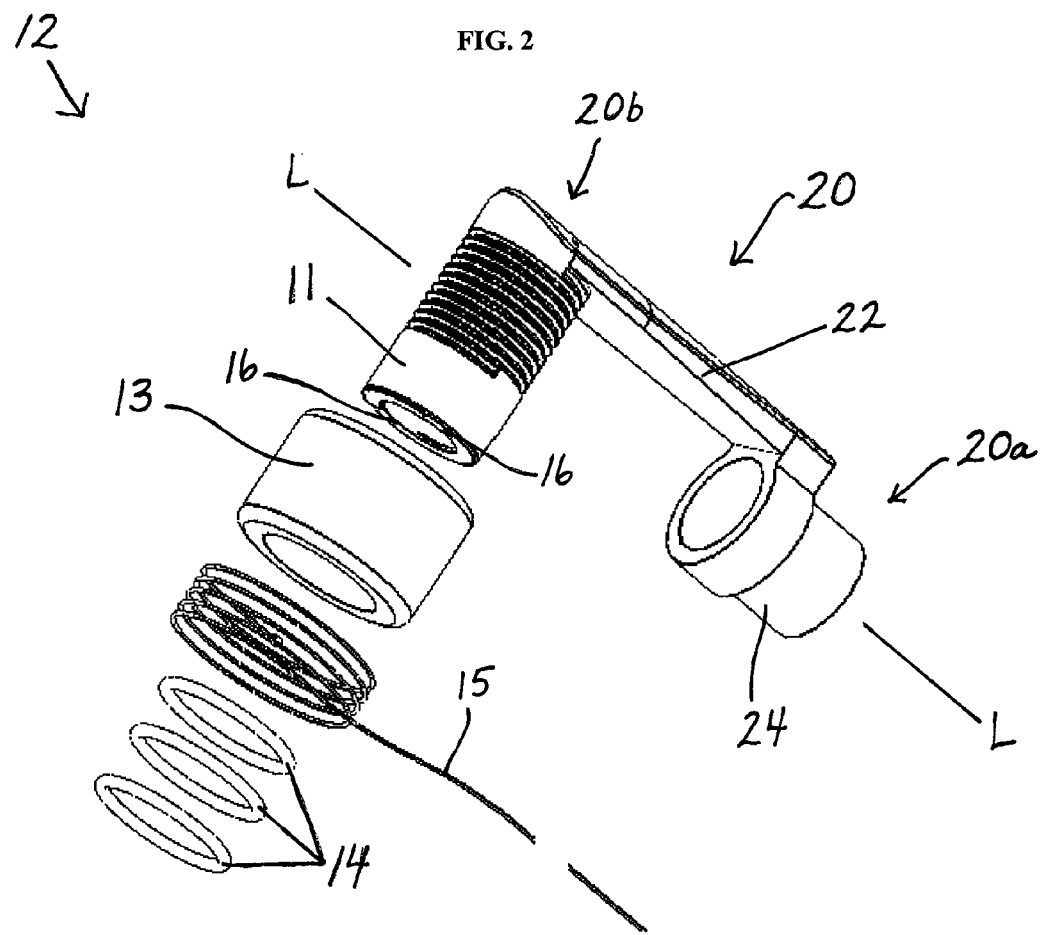
FIG. 2 is an assembly view of the end effector of the ligation and coagulation device shown in FIG. 1.

FIGS. 1 and 2 illustrate one exemplary embodiment of a ligation and coagulation device 10 for use with an endoscope 18 and having an end effector 12, at least one ligation band 14 removably disposed on a portion of the end effector 12, and a pair of electrodes 16 disposed adjacent to each other on a tissue contacting portion of the end effector 12. In the illustrated embodiment, a proximal portion 20a (FIG. 2) of the end effector 12 is adapted to removably mate to a distal end of an endoscope 18 and a distal portion 20b (FIG. 2) of the end effector includes a cylindrical member 11 that is positioned transverse to a longitudinal axis L of the endoscope 18. A pair of spaced electrodes 16 are disposed adjacent to each other on a tissue contacting portion of the cylindrical member 11 and are adapted to coagulate a target region of tissue. The electrodes 16 can be configured to have a variety of shapes, spacing, and sizes. At least one ligation band 14 is removably disposed in a delivery configuration on a portion of the cylindrical member 11, and the band 14 is adapted to be configured in a tissue-engaging configuration upon release from the cylindrical member 11 to thereby ligate the targeted tissue. A cylindrical cap 13 can be rotatably coupled to the cylindrical member 11, and an actuator 15 can be operatively associated with the cap 13 and adapted to rotate the cap 13. In use, rotating the cap 13 is effective to release the at least one ligation band 14 from the cylindrical member 11. The device can thus be used in conjunction with an endoscope 18 to ligate and coagulate a target region of tissue.

Figure 2A:
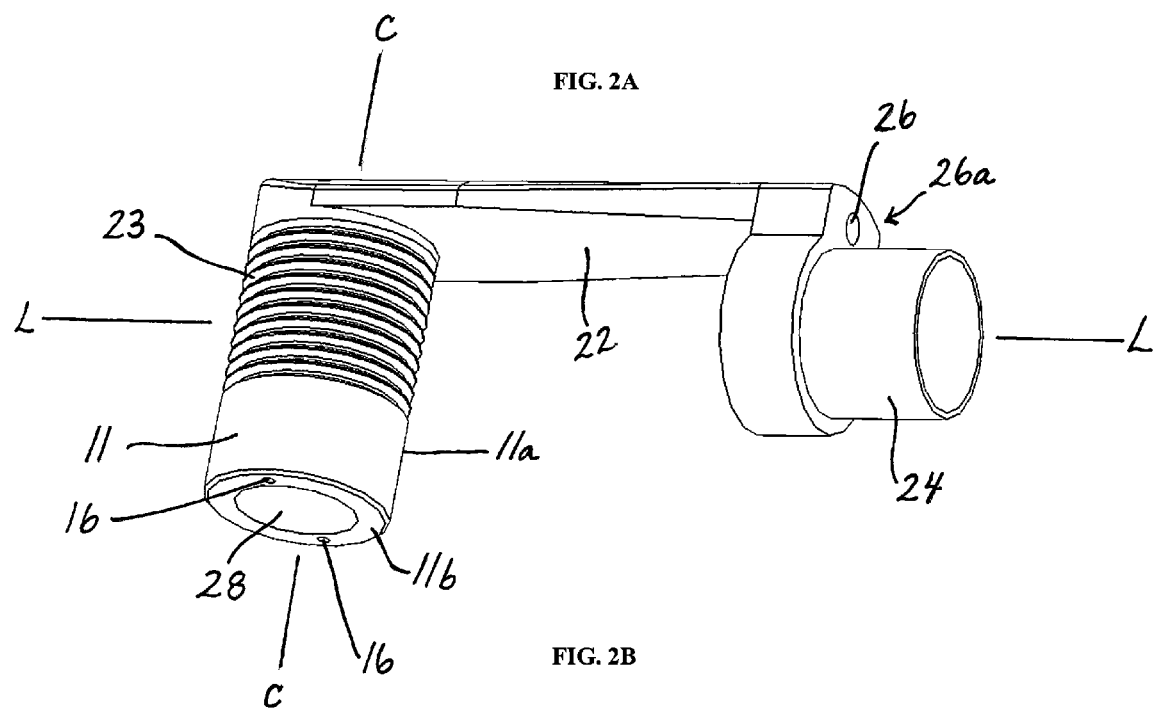
FIG. 2A is a perspective view of the arm and cylindrical member of the end effector shown in FIG. 2.
Figure 2B:
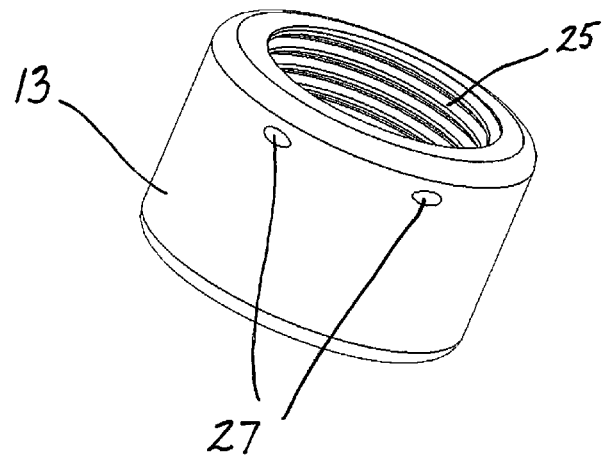
FIG. 2B is a perspective view of the cap of the end effector shown in FIG. 2.
Figure 2C:
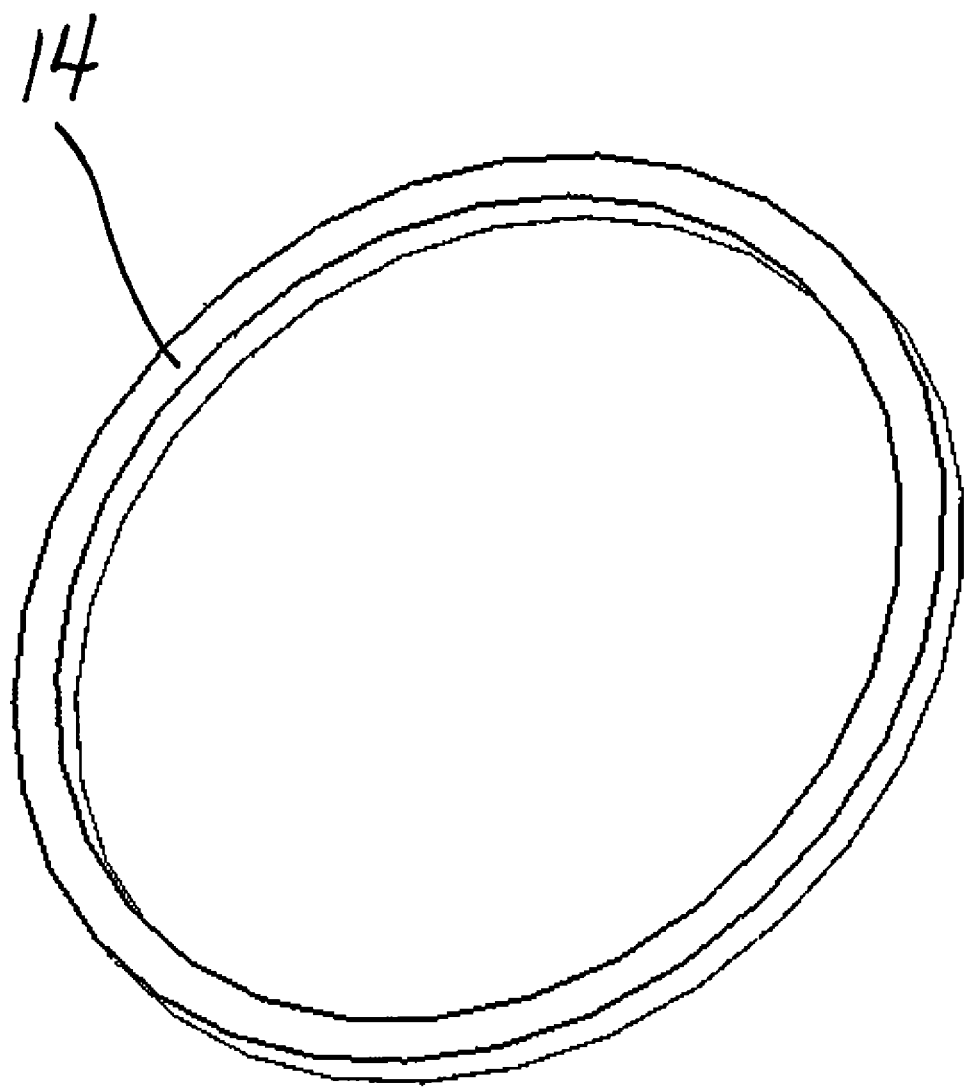
FIG. 2C is a perspective view of one embodiment of a ligation band.
Figure 3:
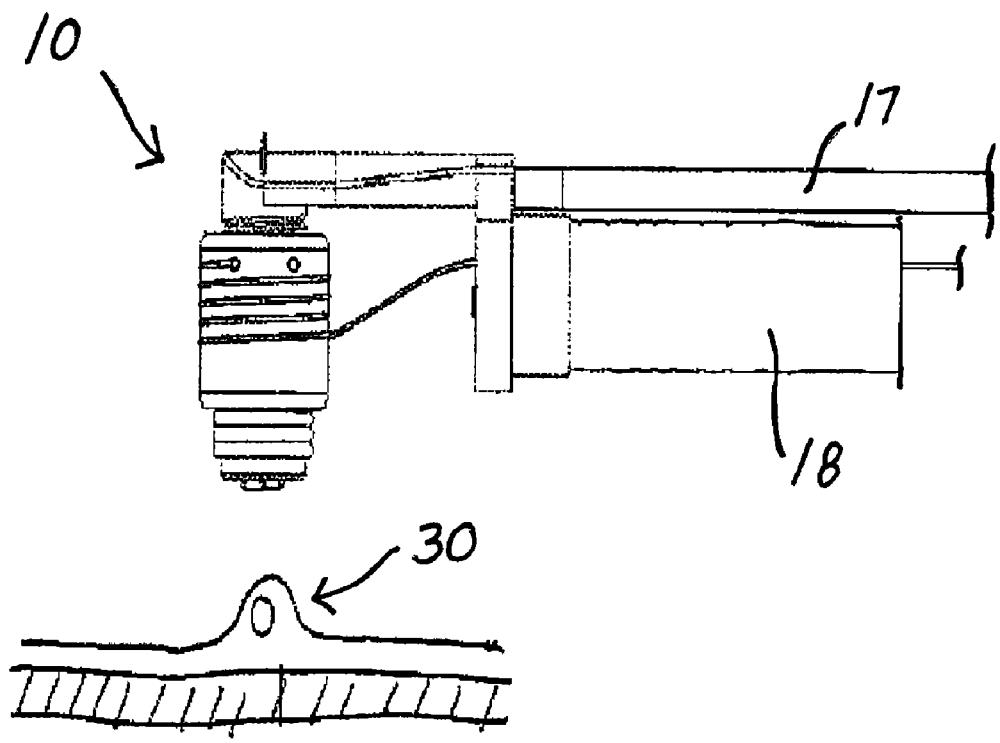
FIG. 3 is a perspective view of the ligation and coagulation device shown in FIG. 1 showing the device positioned adjacent a target region of tissue.

The end effector 12 can have various shapes and sizes, but in one exemplary embodiment, as shown in more detail in FIGS. 2-2C, the end effector 12 is in the form of a frame 20 having a proximal portion 20a that is removably matable to a distal end of an endoscope, an arm 22 that extends from the proximal portion 20a along a longitudinal axis L of the endoscope, and a cylindrical member 11 that is disposed at a distal end 20b of the arm 22 and oriented transverse to the longitudinal axis L of the endoscope. The end effector 12 is shown as a rigid structure, however, the end effector can be movable and adapted to be oriented at a selected angle with respect to a longitudinal axis L of the device. For example, the end effector 12 can be jointed or can include a ratcheting mechanism to facilitate positioning the device. As shown in FIG. 2A, the proximal portion 20a of the end effector 12 is adapted to removably mate to a distal end of an endoscope. In the illustrated embodiment, the proximal portion 20a of the end effector 12 is in the form of a cylindrical collar 24 that is adapted to slidably engage a distal end of an endoscope. Various techniques can be used to secure the end effector 12 to an endoscope such as a snap-fit, interference fit, or threaded engagement. Although the end effector 12 is shown and described in conjunction with an endoscope, a person skilled in the art will appreciate that the end effector 12 can also be removably matable to, formed on or deliverable through an accessory channel or a sleeve slidably disposable over an endoscope.

As further shown in FIG. 2A, the end effector 12 can have an arm 22 extending distally from the cylindrical collar 24. In the illustrated embodiment, the arm 22 connects the proximal and distal portions 20a, 20b of the end effector 12 and extends along the longitudinal axis L of the device. The arm can have a lumen or bore 26 extending therethrough to facilitate fluid delivery and/or suction through the end effector 12. Blood or other debris present during a procedure, for example, can be cleared by means of a fluid delivered under pressure to the surgical site. Suction, for example, can be useful to allow the targeted tissue to be drawn into contact with the end effector 12. In one embodiment shown in FIG. 2A, the proximal end 26a of the bore is adapted to removably mate to a suction line 17 (FIG. 1) that extends proximally from the end effector 12 and is connected to a vacuum source at a proximal end (not shown). The distal end of the bore 26 is associated with a cylindrical member 11 that is described below in detail. Although the arm 22 is shown and described as facilitating suction to draw the targeted tissue into contact with the end effector 12, the arm 22 can also facilitate the introduction of another device for drawing the tissue into contact with the end effector 12. For example, the bore 26 can serve as an entry port for a tissue grasper or other tool.

As indicated above, the distal end of the arm 22 can be associated with a cylindrical member 11. In one exemplary embodiment, illustrated in FIGS. 2 and 2A, the cylindrical member 11 has an outer wall 11a defining a substantially central opening 28. As shown, the cylindrical member 11 extends downward from the arm 22 and is oriented such that the central axis C of the central opening 28 is substantially transverse to the longitudinal axis L of the device. The central opening 28 can also be in communication with the bore 26 that extends through the arm 22. As explained above, this configuration allows the targeted tissue to be drawn into the central opening 28 of the cylindrical member 11 by applying suction to the end effector 12 or an alternative technique such as inserting a tissue grasper. The cylindrical member 11 can also include a pair of spaced electrodes 16 disposed adjacent to each other on a distal surface 11b of the outer wall 11a. In an exemplary embodiment, the electrodes 16 are in a co-planar, parallel arrangement. Such a configuration encourages deeper, submucosal tissue damage which works to prevent the recurrence of the defect being treated. The co-planar arrangement can also reduce adhesion of the treated tissue to the electrodes 16. The electrodes 16 can also be positioned such that they are in contact with the targeted tissue when the vacuum source or other means is activated to draw the tissue into the central opening 28 of the end effector 12. The electrodes 16 can be in communication with a current source (not shown) such that they can be selectively energized to coagulate the targeted tissue. Various current sources can be used to energize the electrodes 16. For example, in one exemplary embodiment, the electrodes 16 can be in communication with an RF generator. As shown in FIGS. 2 and 2A, the cylindrical member 11 can further include threads 23 formed on a portion of an outer surface thereof. The threads 23 can be adapted to mate with complementary threads 25 formed on an inner surface of a cylindrical cap 13 which is discussed in more detail below. In an exemplary embodiment, the threads 23 are formed on the portion of the cylindrical member 11 that is adjacent to the arm 22 of the end effector 12. The non-threaded portion of the cylindrical member 11 can be adapted to support at least one ligation band 14 in a delivery configuration.

At least one ligation band 14 can be disposed in a delivery configuration (e.g., a configuration having an expanded diameter) on a portion of the end effector 12 and be adapted to be configured in a tissue-engaging configuration (e.g., a configuration having a reduced diameter) upon release from the end effector 12. In one exemplary embodiment, shown in FIG. 1, multiple bands 14 are disposed on the non-threaded portion of the cylindrical member 11 adjacent the target region of tissue. In the embodiment illustrated in FIGS. 1, 2, and 2C, the ligation band 14 takes the form of an elastic, O-shaped ring. However, the ligation band 14 can be any shape and size so long as it can be disposed on a portion of the end effector 12 and engage tissue upon release from the end effector 12.

As indicated above, a cap 13 can be rotatably coupled to the cylindrical member 11. The cap 13 can have various shapes and sizes, but in one exemplary embodiment, as shown in FIGS. 1 and 2, the cap is in the form of a hollow cylinder having threads 25 formed on an inner surface thereof. The threads 25 formed on the inner surface of the cap 13 can be adapted to mate with the threads 23 formed on the outer surface of the cylindrical member 11, and the cap 13 can be sized such that it can be rotatably coupled to the cylindrical member 11. The cap 13 and cylindrical member 11 can be configured such that rotating the cap 13 is effective to release at least one ligation band 14 from the end effector 12. Various configurations and techniques can be used to release at least one ligation band 14, but in one embodiment the cap 13 can be rotated with respect to the cylindrical member 11. By rotating the cap 13, the cap 13 can be advanced along the cylindrical member 11 until it comes into contact with at least one ligation band 14, which is positioned distally of the cap. Further advancement of the cap 13 is effective to push the ligation band 14 off of the end effector 12 and into a tissue-engaging configuration where the band 14 is disposed around the target region of tissue. Interruptions in the smooth surfaces of the threads in the cap can be employed to detent the releases of individual ligating bands and provide tactile feedback to the user.

The end effector 12 can further include an actuator 15 that is operatively associated with the cap 13 and effective to rotate the cap 13 upon actuation. A variety of mechanisms can be used to rotate the cap 13, but in one embodiment, shown in FIGS. 1 and 2, the actuator 15 is in the form of a pull wire 15 that is wound around the cap 13. A distal end of the pull wire 15 can be fixed to the cap 13 by, for example, achieving an interference fit between the wire 15 and a cutout 27 in the cap 13. A proximal portion of the wire can extend proximally from the cap such that it can be manipulated by a user. While the device is shown with a pull wire 15, a person skilled in the art will appreciate that the actuator 15 can also be in the form of a cable, braided rope, or other flexible cord. The actuator 15 can be made from any flexible material suitable for being wound around the cap 13. In use, the actuator can slide along the longitudinal axis L of the device, and the axial force can be converted to a rotational force to cause the cap 13 to rotate.

Figure 4:
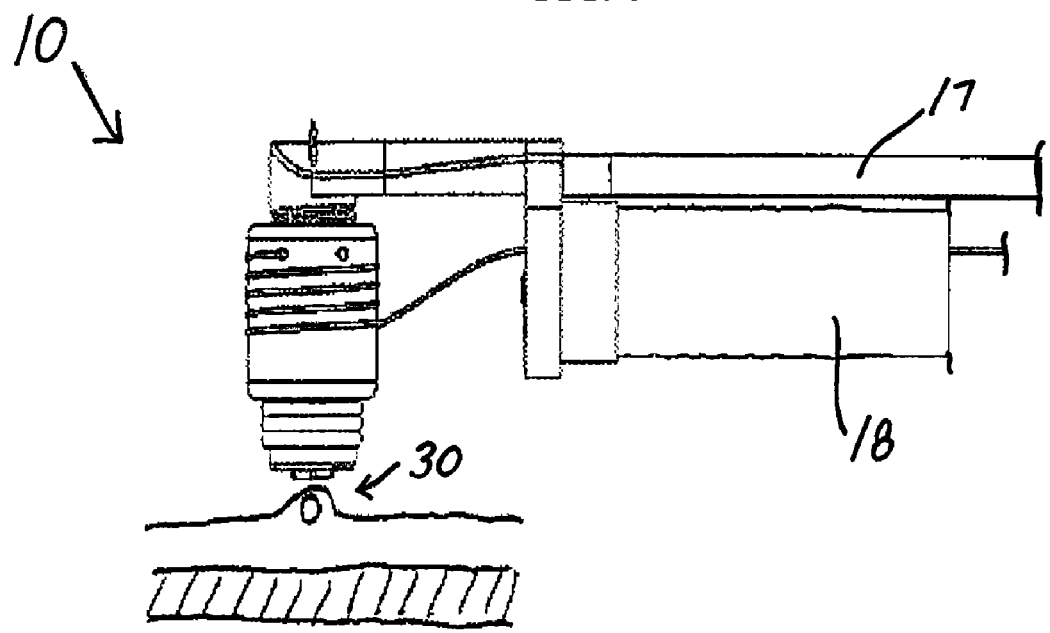
FIG. 4 is a perspective view of the ligation and coagulation device shown in FIG. 1 showing the targeted tissue being drawn into the central opening of the end effector shown in FIG. 2.
Figure 5:
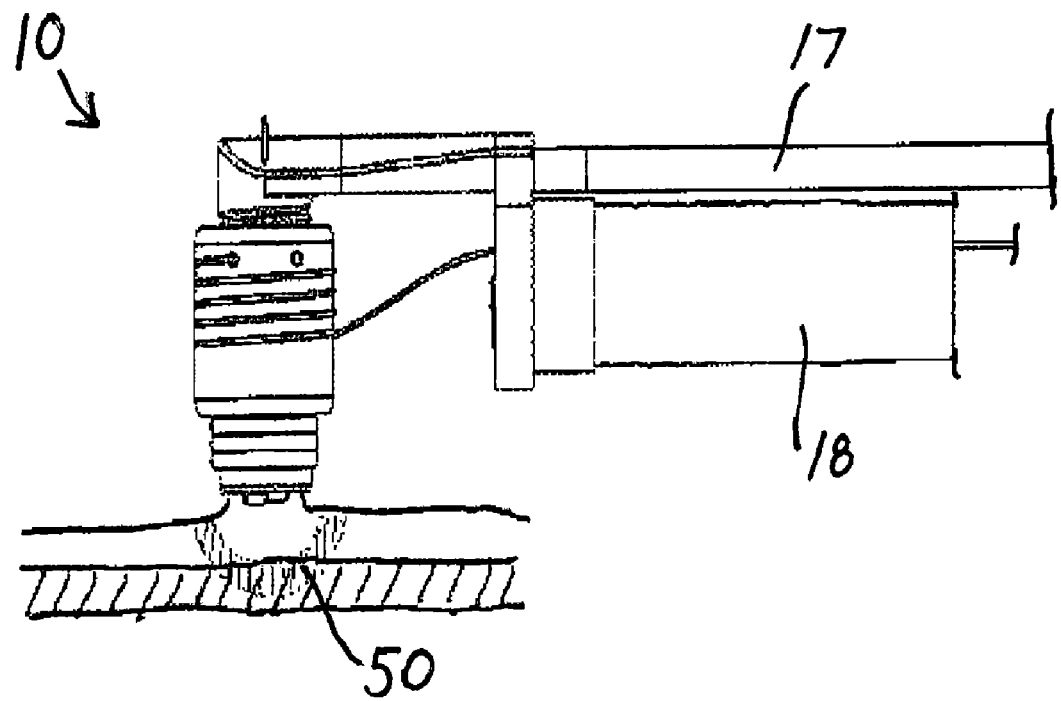
FIG. 5 is a perspective view of the ligation and coagulation device shown in FIG. 1 showing current being applied to the targeted tissue.
Figure 6:
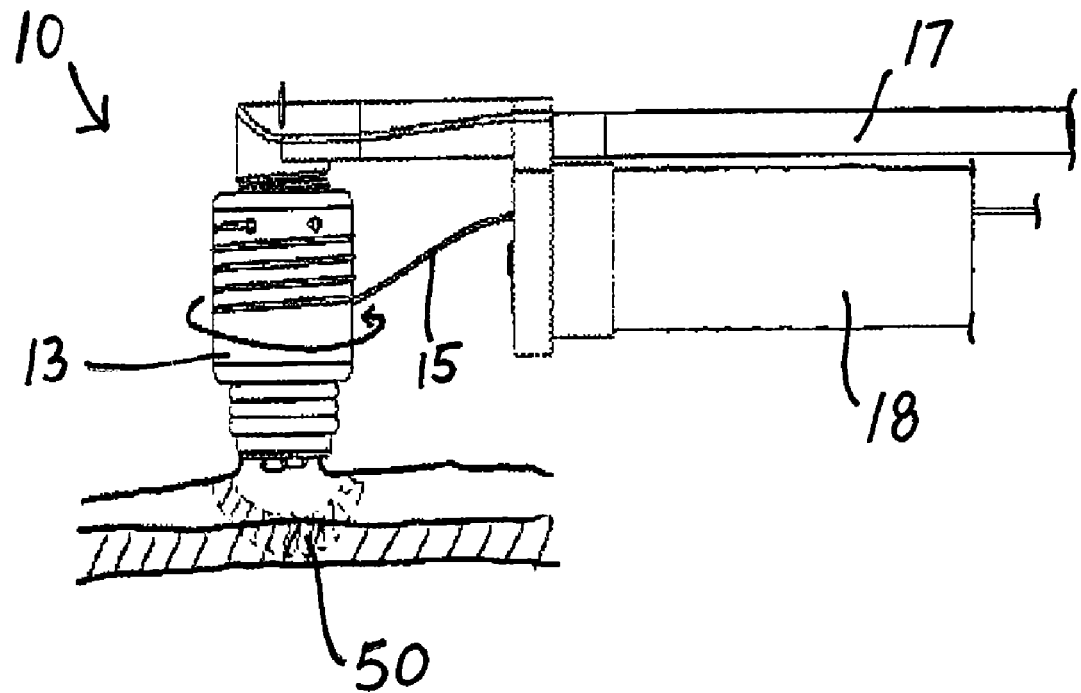
FIG. 6 is a perspective view of the ligation and coagulation device shown in FIG. 1 showing the cap shown in FIG. 2B being rotated.
Figure 7:
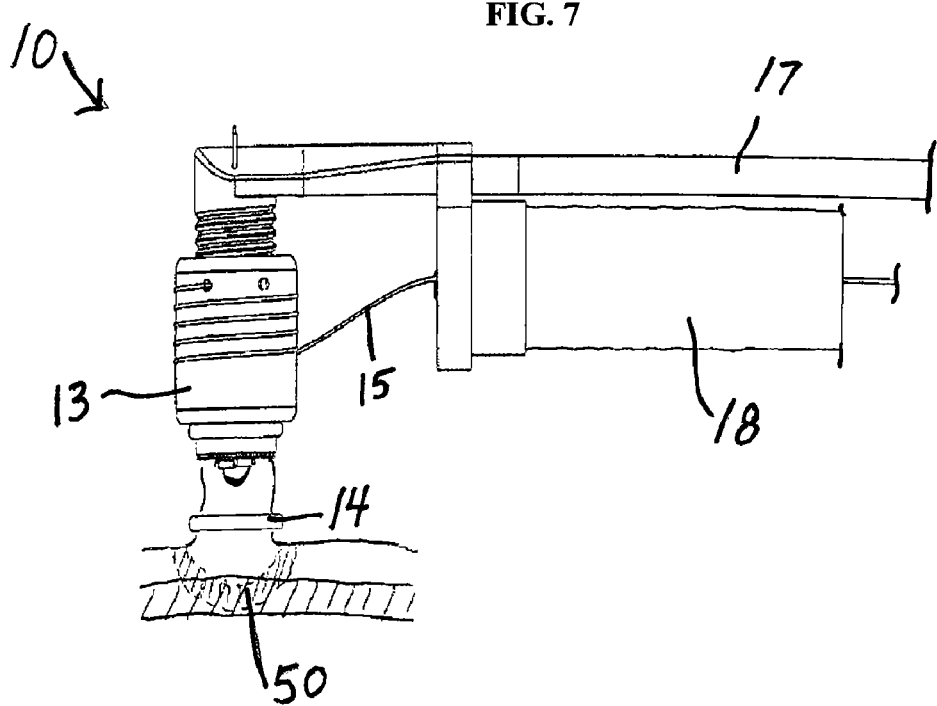
FIG. 7 is a perspective view of the ligation and coagulation device shown in FIG. 1 showing the ligation band shown in FIG. 2C being deployed.
Figure 8:
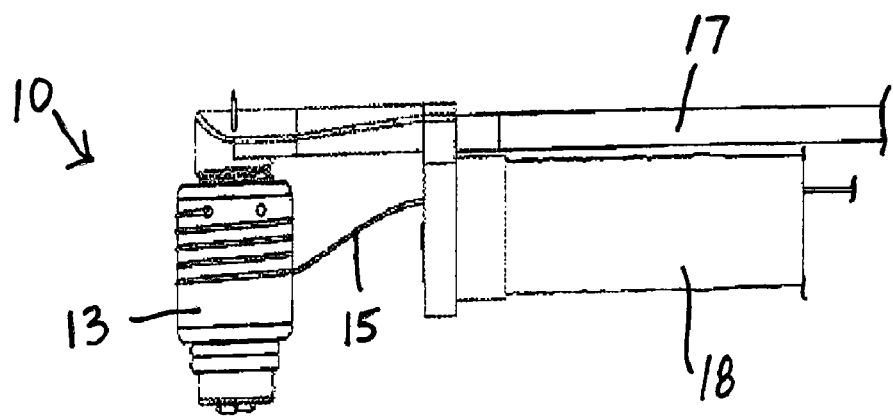
FIG. 8 is a perspective view of the ligation and coagulation device shown in FIG. 1 showing the device being removed from the treated tissue.
Figure 8:
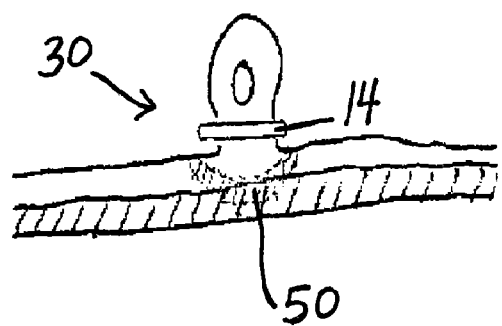

The present invention also provides methods for ligating and coagulating a target region of tissue. In one exemplary embodiment, shown in FIGS. 3-8, the ligation/coagulation device 10 can be mated to a distal end of an endoscope 18, and the endoscope 18 can be inserted translumenally and positioned adjacent the target region of tissue 30. Once the device 10 is positioned in the body proximate to the procedure site (e.g., positioned adjacent a varix or hemorrhoid), a fluid such as water or saline can be injected through the suction line 17 to clear the area of blood or other debris. As shown in FIG. 4, the target tissue 30 can be drawn into the central opening of the end effector by activating the vacuum source (not shown). Once the target tissue 30 is captured within the end effector, as illustrated in FIG. 5, current can be delivered through the electrodes to thereby coagulate the tissue. FIG. 5 shows the deep, submucosal tissue damage 50 resulting from the parallel electrode arrangement described above. With the target tissue still captured within the end effector, at least one ligation band can be deployed to thereby ligate the tissue. As shown in FIG. 6, force can be applied to the pull wire 15 to rotate the cap 13 with respect to the cylindrical member. FIG. 7 illustrates that continued rotation of the cap 13 is effective to push at least one ligation band 14 off of the end effector and into a tissue-engaging configuration (e.g., having a reduced diameter) where the band 14 is disposed around the target region of tissue 30. Although the procedure is shown and described as coagulation followed by ligation, a person skilled in the art will appreciate that ligation can occur before coagulation or the two can occur simultaneously. As shown in FIG. 8, once the coagulation and/or ligation is complete, the vacuum source can be deactivated and the device can be removed. The treated tissue 30, including the defect, will eventually slough off leaving fibrous tissue in place and preventing the reformation of such a defect.

Figure 9:
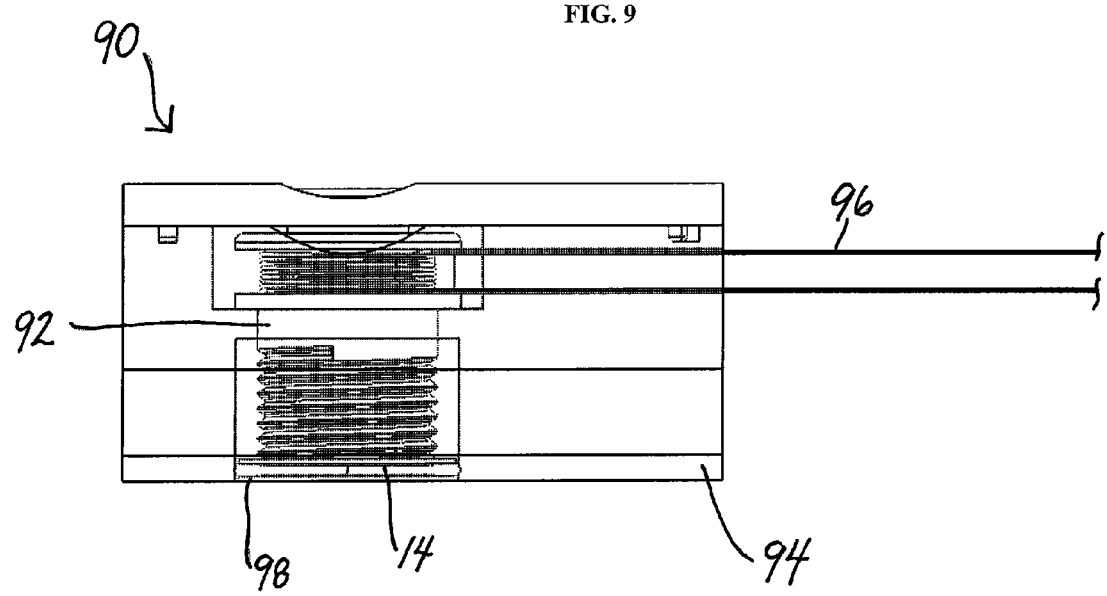
FIG. 9 is a cross-sectional view of one embodiment of an end effector.
Figure 10:
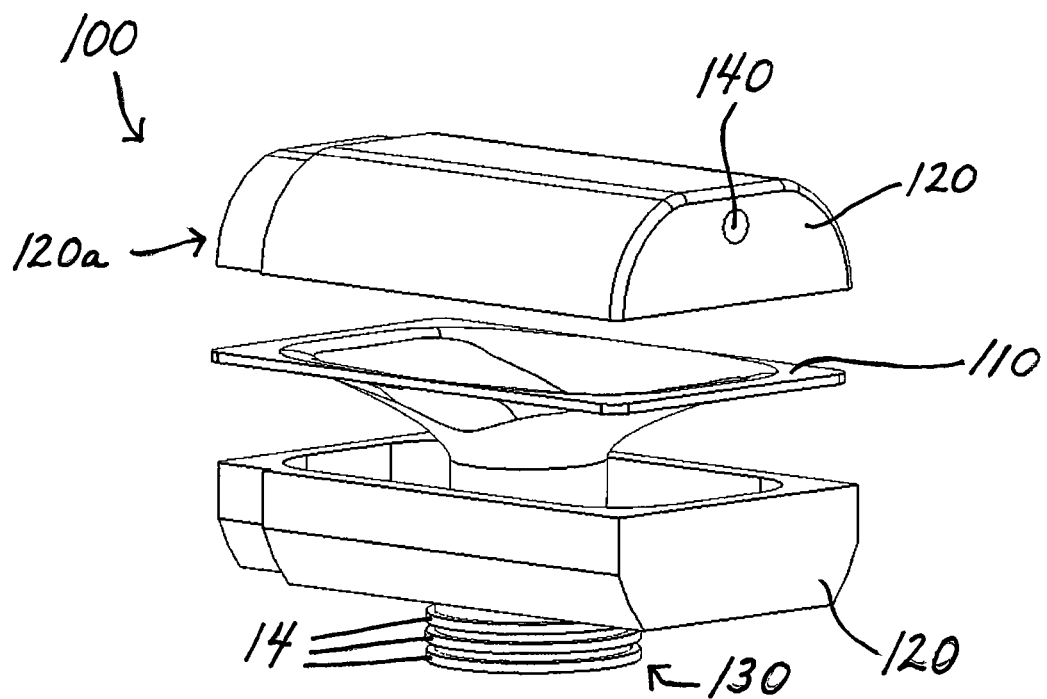
FIG. 10 is a perspective view of another embodiment of an end effector.
Figure 10A:
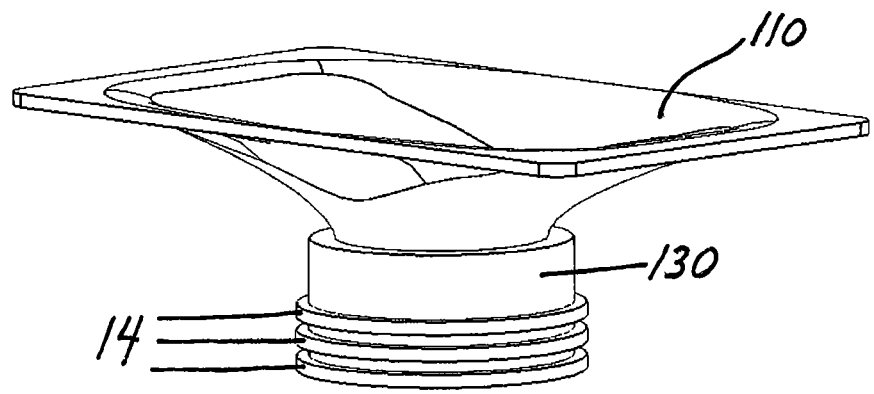
FIG. 10A is a perspective view of the flexible membrane of the end effector shown in FIG. 10.

As indicated above, the end effector can have various configurations. FIGS. 9-10A illustrate additional exemplary end effector embodiments. As shown in FIG. 9, the end effector 90 can include a cylindrical member 92 that is rotatably disposed within a housing 94, an actuator 96 that is operatively associated with the cylindrical member 92, a frangible ring 98 that is threadably coupled to the cylindrical member 92 and is adapted to support a ligation band 14 in a delivery configuration, and a pair of electrodes disposed on a distal surface of the end effector 90.

Figure 9A:
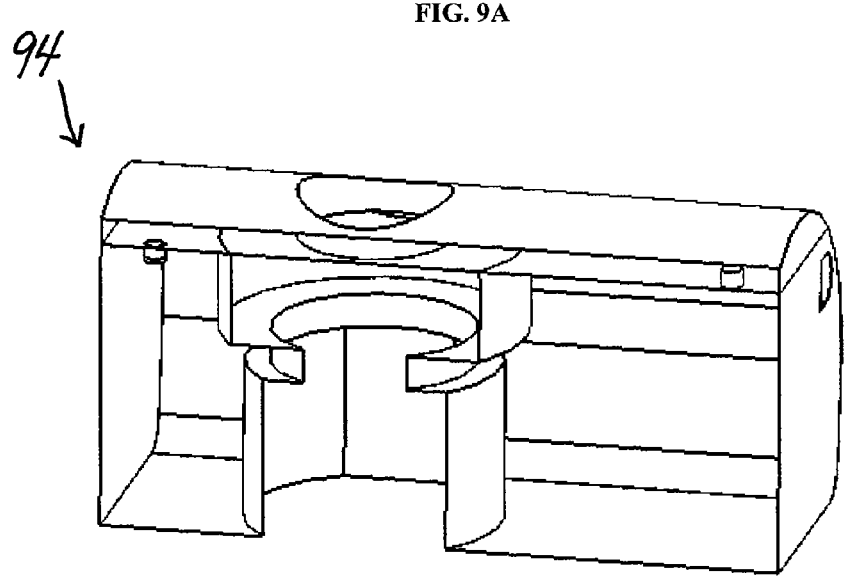
FIG. 9A is a cross-sectional view of the housing of the end effector shown in FIG. 9.

The housing 94 can have various configurations, but in one exemplary embodiment, shown in FIGS. 9 and 9A, the housing 94 is formed to fit around the cylindrical member 92 such that the cylindrical member 92 is supported by the housing 94 but allowed to rotate within the housing 94. The housing 94 can be formed on, attached to, or removably matable to or deliverable through a distal end of an endoscope, accessory channel adapted to mate to an endoscope, or sleeve adapted to mate to an endoscope and/or accessory channel. For example, in one embodiment, the housing 94 can include an arm (not shown) that extends proximally from the housing and which has a cylindrical collar disposed at a proximal end that is adapted to slidably engage a distal end of an endoscope. Various techniques can be used to secure the collar to an endoscope such as a snap-fit, interference fit, or threaded engagement. In another embodiment, the housing 94 can include an opening formed from a resilient material to accommodate a press-fit between an endoscope and the housing. The opening can also be sized to provide a loose fit between the end effector and an endoscope and a set screw can be used to secure the end effector to the endoscope. The housing 94 can also include a plurality of openings to facilitate a connection to a fluid delivery and/or a suction line, a release of one or more ligation bands, an introduction of an actuator, and/or a connection to a current source.

Figure 9B:
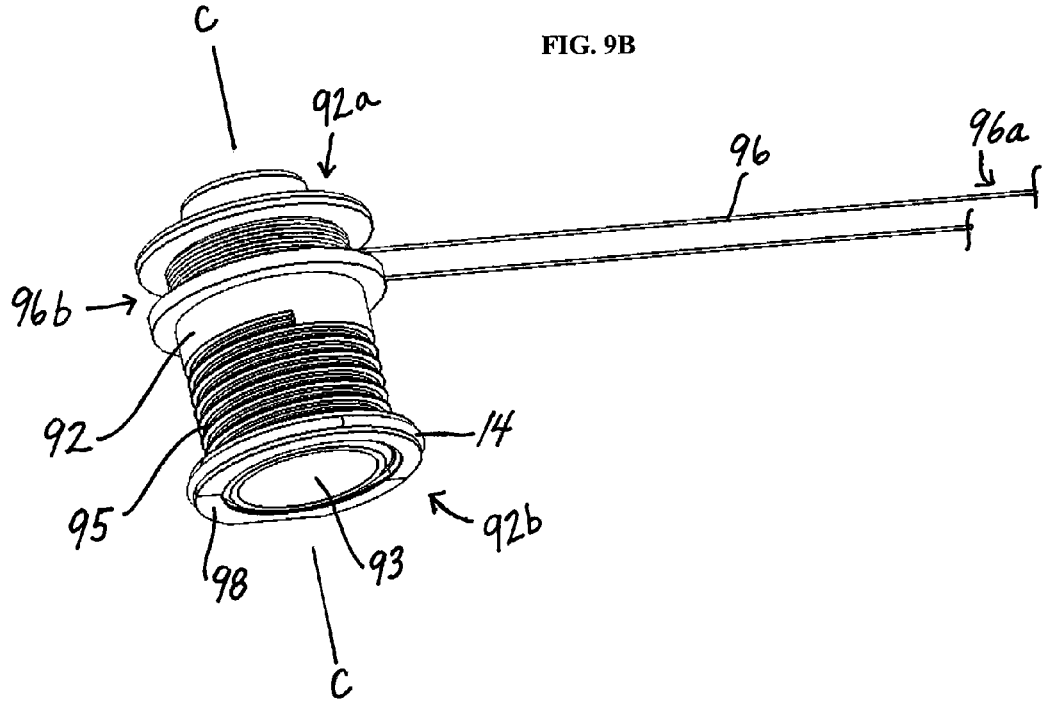
FIG. 9B is a perspective view of the cylindrical member of the end effector shown in FIG. 9.

The actuator 96 can also have a variety of configurations, but as indicated above, in an exemplary embodiment, the actuator 96 is operatively associated with the cylindrical member 92. As shown in FIGS. 9 and 9B, the actuator 96 is in the form of a pull wire 96 having a distal portion 96b that is wound around the cylindrical member 92 and a proximal portion 96a that extends out of the housing 94 and to the user (not shown). While the device is shown with a pull wire 96, a person skilled in the art will appreciate that the actuator 96 can also be in the form of a cable, braided rope, or other flexible cord. Further, the actuator can be in the form of an electro-mechanical component. The actuator 96 can be made from any flexible material suitable for being wound around the cylindrical member 92. To increase friction between the cylindrical member 92 and the actuator 96 and to prevent the actuator 96 from slipping, the cylindrical member 92 can include a sticky or textured surface and/or the actuator 96 can be wound around the cylindrical member 92 multiple times. In use, the actuator 96 can slide along the longitudinal axis of the device, and the axial force can be converted to a rotational force to case the cylindrical member to rotate within the housing.

FIGS. 9 and 9B illustrate one exemplary embodiment of the cylindrical member 92. As shown, the cylindrical member 92 has an outer wall defining a substantially central opening 93 and is oriented in the housing 94 such that the central axis C of the central opening 93 is substantially transverse to the longitudinal axis of the device. The central opening 93 can also be in communication with a fluid delivery and/or a suction line. The suction line feature is useful to enable the targeted tissue can be drawn into the central opening 93 of the cylindrical member 92. In other embodiments, tissue can be drawn into the central opening 93 by inserting a tissue grasper or other tool through the central opening 93. As indicated above, a proximal portion 92a of the cylindrical member 92 can be operatively associated with the actuator 96 such that applying force to the actuator 96 is effective to rotate the cylindrical member 92 within the housing 94. A distal portion of the cylindrical member 92b can have threads 95 formed on an outer surface thereof for mating with complementary threads 99 formed on a frangible ring 98.

Figure 9C:
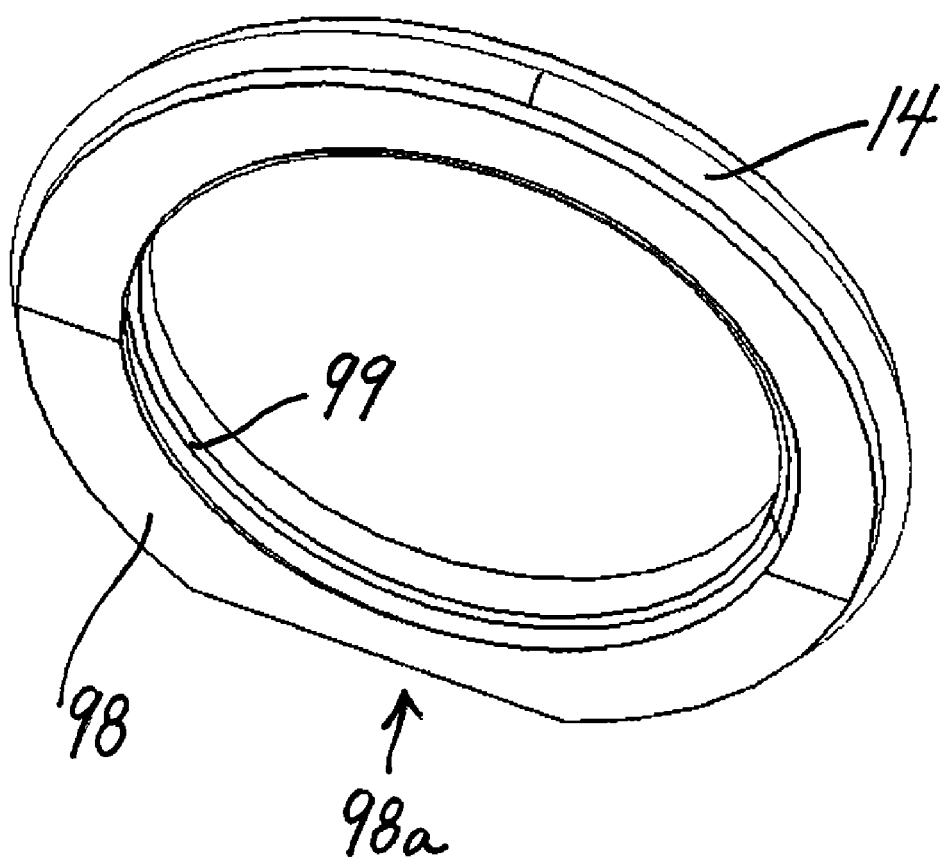
FIG. 9C is a perspective view of the frangible ring disposed on the cylindrical member shown in FIG. 9B.

The frangible ring 98 is preferably configured to threadably mate to the cylindrical member 92 and support at least one ligation band 14 in its expanded condition. As shown in FIGS. 9, 9B, and 9C, a ligation band 14 is disposed in a delivery configuration (e.g., expanded diameter) on the frangible ring 98. The frangible ring 98 can have threads 99 formed on an inner surface thereof for mating with the threads 95 formed on the cylindrical member 92. The frangible ring 98 can have a variety of configurations, but in an exemplary embodiment, shown in FIG. 9C, the frangible ring 98 is sized and shaped such that it fits snugly within the housing 94 and cannot rotate with respect to the housing 94. As shown, the frangible ring 98 is substantially round but can include a flat portion 98a that corresponds to a similarly shaped portion of the housing 94 and is effective to prevent the ring 98 from rotating within the housing 94. In use, the actuator 96 can be used to rotate the cylindrical member 92 with respect to the frangible ring 98. The housing 94 can work to hold the frangible ring 98 in a fixed position thereby allowing the cylindrical member 92 to be threadably decoupled from the frangible ring 98. The frangible ring 98 can be configured such that upon release from the cylindrical member 92 the ring 98 collapses under the stress applied by the ligation band 14 and the band 14 engages the targeted tissue. The frangible ring 98 can be formed of a material adapted to be absorbed by the body or the ring can simply be passed by the patient.

As with the embodiments described above, the end effector shown in FIGS. 9-9C can also include a pair of spaced electrodes disposed adjacent to each other on a distal facing surface. The electrodes can be disposed on a variety of distal facing surfaces. For example, the electrodes can be disposed on the housing, cylindrical member, or frangible ring. In an exemplary embodiment, the electrodes are in a co-planar, parallel arrangement and can be positioned such that they are in contact with the target region of tissue when the targeted tissue is drawn into the central opening of the end effector. The electrodes can also be in communication with a current source (not shown) such that they can be selectively energized to coagulate the targeted tissue. Various current sources can be used to energize the electrodes. For example, in one exemplary embodiment, the electrodes can be in communication with an RF generator.

FIGS. 10 and 10A illustrate another exemplary embodiment of an end effector 100 having a flexible membrane 110 that is adapted to release at least one ligation band 14. As shown, the end effector 100 includes a housing 120, a flexible membrane 110, and a collar 130 having at least one ligation band 14 and a pair of electrodes disposed thereon. The housing 120 can have various configurations, but in one exemplary embodiment, shown in FIG. 10, the housing 120 is sized and shaped to support the collar 130 and flexible membrane 110 but allow the collar 130 and membrane 110 to move in a direction that is transverse to the longitudinal axis of the device. The collar 130 can be operatively associated with the flexible membrane 110 such that the two elements move together as a unit. FIG. 10 illustrates that the flexible membrane 110 and collar 130 are seated within the housing 120 with a portion of the collar 130 extending through an opening in a bottom facing surface of the housing. This opening can be sized such that it is large enough for the collar 130 to easily move in and out of the housing 120 but small enough to prevent any ligation bands 14 disposed on the collar 130 from passing into the housing 120. The housing 120 can also include an opening 140 on a proximal facing surface to facilitate a connection to a suction line. As with the housing described above, the housing 120 shown in FIG. 10 can be formed on, attached to, or removably matable to or deliverable through a distal end of an endoscope, accessory channel adapted to mate to an endoscope, or sleeve adapted to mate to an endoscope and/or accessory channel. In use, a vacuum source (not shown) can be activated to cause the flexible membrane 110 and collar 130 to move toward an upper portion 120a of the housing 120. As the collar 130 is pulled upward, the housing 120 acts against the ligation bands 14 disposed on the collar 130 to release at least one band 14 from the collar 130 and thereby engage the targeted tissue. As with the above embodiments, the electrodes disposed on the collar can be used to coagulate the targeted tissue before, after, or during the ligation step.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   an end effector configured to access tissue to be treated at a surgical site comprising a cylindrical member having an outer wall defining a substantially central opening;
   at least one ligation band removably disposed in a delivery configuration on a portion of the end effector, the ligation band being adapted to be configured in a tissue-engaging configuration upon release from the end effector; and
   a pair of spaced electrodes disposed adjacent to each other on a tissue contacting portion of the end effector, wherein the electrodes are disposed on a distal surface of the outer wall.

2. The device of claim 1, wherein the end effector is removably associated with an endoscope such that a central axis of the central opening is substantially transverse to a longitudinal axis of the endoscope.

3. The device of claim 1, further comprising a suction line adapted to draw tissue into the central opening.

4. The device of claim 1, wherein the end effector is movable and adapted to be oriented at a selected angle with respect to a longitudinal axis of the device.

5. The device of claim 1, wherein the at least one ligation band comprises an elastic ring.

6. The device of claim 1, wherein the electrodes are in communication with a current source.

7. The device of claim 6, wherein the current source is adapted to be selectively energized.

8. The device of claim 1, wherein a cylindrical cap is rotatably coupled to the cylindrical member such that rotating the cap is effective to release the at least one ligation band from the end effector.

9. The device of claim 8, further comprising an actuator operatively associated with the cap and adapted to rotate the cap.

10. The device of claim 9, wherein the actuator comprises a pull wire having a portion that is wound around the cap and a proximally extending portion that is able to be manipulated by a user.

11. A surgical device, comprising:
an end effector configured to access tissue to be treated at a surgical site;
at least one ligation band removably disposed in a delivery configuration on a portion of the end effector, the ligation band being adapted to be configured in a tissue-engaging configuration upon release from the end effector, wherein the at least one ligation band is supported in its expanded condition by a frangible ring; and
a pair of spaced electrodes disposed adjacent to each other on a tissue contacting portion of the end effector.

12. The device of claim 11, wherein the frangible ring is threadably coupled to the end effector and adapted to collapse under the stress applied by the ligation band upon release from the end effector.

13. The device of claim 11, wherein the electrodes are disposed on a portion of the frangible ring.

14. A surgical device, comprising:
an end effector configured to access tissue to be treated at a surgical site;
at least one ligation band removably disposed in a delivery configuration on a portion of the end effector, wherein the end effector includes a flexible membrane adapted to release the at least one ligation band, the ligation band being adapted to be configured in a tissue-engaging configuration upon release from the end effector; and
a pair of spaced electrodes disposed adjacent to each other on a tissue contacting portion of the end effector.

15. A method of ligating and coagulating tissue, comprising:
inserting an end effector translumenally, the end effector having an outer wall defining an opening, one or more ligation bands disposed on a portion thereof, and a pair of spaced, adjacent electrodes disposed on a tissue contacting portion thereof;
positioning the end effector adjacent a target region of tissue;
drawing the target tissue into the opening;
deploying at least one of the ligation bands to the target tissue to ligate the target tissue; and
delivering current to the target tissue through the electrodes to thereby coagulate the target tissue, wherein deploying at least one of the ligation bands and delivering current to the target tissue occur simultaneously.

16. The method of claim 15, wherein drawing the target tissue into the opening is effected by applying suction to the tissue.

17. The method of claim 15, wherein deploying at least one of the ligation bands comprises actuating a cylindrical cap threadably coupled to the end effector.

18. The method of claim 17, wherein actuating the cylindrical cap comprises rotating the cap using a pull wire wound around the cap.

19. The method of claim 15, wherein deploying at least one of the ligation bands and delivering current to the target tissue occur sequentially.

20. The method of claim 15, further including the step of sterilizing said device after at least one use.

21. A surgical device, comprising:
an end effector having a lumen formed therein, the end effector being configured to access tissue to be treated at a surgical site;
at least one ligation band removably disposed in a delivery configuration on a portion of the end effector, the ligation band being adapted to be configured in a tissue-engaging configuration upon release from the end effector; and
a pair of spaced electrodes disposed adjacent to each other on a tissue contacting portion of an inner wall of the end effector.

22. A surgical device, comprising:
an end effector configured to access tissue to be treated at a surgical site;
at least one ligation band removably disposed in a delivery configuration on a portion of the end effector, the ligation band being adapted to be configured in a tissue-engaging configuration upon release from the end effector; and
a pair of spaced electrodes disposed adjacent to each other on a tissue contacting portion of a distal facing surface of the end effector.

* * * * *

UNITED STATES PATENT AND TRADEMARK OFFICE
CERTIFICATE OF CORRECTION

PATENT NO.      : 7,641,652 B2
APPLICATION NO. : 11/427598
DATED           : January 5, 2010
INVENTOR(S)     : Coe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 510 days.

Signed and Sealed this

Sixteenth Day of November, 2010

David J. Kappos
*Director of the United States Patent and Trademark Office*